United States Patent
Santek

(10) Patent No.: US 10,616,698 B2
(45) Date of Patent: Apr. 7, 2020

(54) FIXATION OF A BONE CONDUCTION FLOATING MASS TRANSDUCER

(71) Applicant: MED-EL Elektromedizinische Geraete GmbH, Innsbruck (AT)

(72) Inventor: Michael Santek, Innsbruck (AT)

(73) Assignee: MED-EL Elektromedizinische Geraete GmbH, Innsbruck (AT)

( * ) Notice: Subject to any disclaimer, the term of this patent is extended or adjusted under 35 U.S.C. 154(b) by 137 days.

(21) Appl. No.: 15/553,595

(22) PCT Filed: Mar. 17, 2016

(86) PCT No.: PCT/US2016/022732
§ 371 (c)(1),
(2) Date: Aug. 25, 2017

(87) PCT Pub. No.: WO2016/149434
PCT Pub. Date: Sep. 22, 2016

(65) Prior Publication Data
US 2018/0249262 A1      Aug. 30, 2018

Related U.S. Application Data

(60) Provisional application No. 62/134,626, filed on Mar. 18, 2015.

(51) Int. Cl.
*H04R 25/00*    (2006.01)
*A61F 2/28*    (2006.01)

(52) U.S. Cl.
CPC ............ *H04R 25/606* (2013.01); *A61F 2/28* (2013.01); *H04R 25/60* (2013.01)

(58) Field of Classification Search
CPC .. A61F 2002/183; A61F 11/04; A61F 11/045; H04R 25/60; H04R 25/604
(Continued)

(56) References Cited

U.S. PATENT DOCUMENTS

| 4,612,915 A | 9/1986 | Hough et al. |
| 8,241,201 B2 | 8/2012 | Hakansson |

(Continued)

FOREIGN PATENT DOCUMENTS

| WO | WO 2013/054312 | 4/2013 |
| WO | WO 2014/138149 | 9/2014 |

OTHER PUBLICATIONS

European Patent Office, Extended European Search Report, Application No. 16765704.8, dated Feb. 15, 2018, 9 pages.
(Continued)

*Primary Examiner* — Samuel G Gilbert
(74) *Attorney, Agent, or Firm* — Sunstein LLP

(57) ABSTRACT

An implantable bone conduction transducer has a center rotational axis radially surrounded by an outer surface, and at least one radial projection projecting radially outward from the outer surface. An implantable transducer receptacle has a receptacle outer surface configured to fit into a receptacle recess in skull bone of a recipient patient, a receptacle inner surface configured to fit around the outer surface of the transducer, and at least one projection bracket projecting radially inward away from the receptacle inner surface. The at least one projection bracket and the at least one radial projection are configured to cooperate so that rotation of the transducer around the center rotational axis creates increased lateral force between the transducer and the skull bone surrounding the receptacle recess so as to securely engage the transducer with the skull bone.

18 Claims, 4 Drawing Sheets

(58) Field of Classification Search
USPC .............................................. 600/25; 381/326
See application file for complete search history.

(56) References Cited

U.S. PATENT DOCUMENTS

| | | | |
|---|---|---|---|
| 10,219,060 B2* | 2/2019 | Koper | A42B 3/306 |
| 2007/0173844 A1 | 7/2007 | Ralph et al. | |
| 2010/0305677 A1 | 12/2010 | Schmidt et al. | |
| 2012/0095527 A1 | 4/2012 | Vardi et al. | |
| 2012/0101514 A1 | 4/2012 | Keady et al. | |
| 2012/0271097 A1 | 10/2012 | Ball et al. | |
| 2013/0329918 A1 | 12/2013 | Kubba | |
| 2013/0345495 A1 | 12/2013 | Santek | |

OTHER PUBLICATIONS

International Searching Authority, International Search Report—International Application No. PCT/US2016/022732, dated Jun. 9, 2016 together with the Written Opinion of the International Searching Authority, 13 pages.

* cited by examiner

FIXATION OF A BONE CONDUCTION FLOATING MASS TRANSDUCER

This application is a national phase entry of Patent Cooperation Treaty Application PCT/US2016/022732, filed Mar. 17, 2016, which in turn claims priority from U.S. Provisional Patent Application 62/134,626, filed Mar. 18, 2015, both of which are incorporated herein by reference in their entireties.

FIELD OF THE INVENTION

The present invention relates to hearing implants, and more specifically to fixation of a bone conduction floating mass transducer to a patient's skull bone.

BACKGROUND ART

A normal ear transmits sounds as shown in FIG. 1 through the outer ear 101 to the tympanic membrane (eardrum) 102, which moves the ossicles of the middle ear 103 (malleus, incus, and stapes) that vibrate the oval window 106 and round window 107 membranes of the cochlea 104. The cochlea 104 is a long narrow duct wound spirally about its axis for approximately two and a half turns. It includes an upper channel known as the scala vestibuli and a lower channel known as the scala tympani, which are connected by the cochlear duct. The cochlea 104 forms an upright spiraling cone with a center called the modiolar where the spiral ganglion cells of the cochlear nerve 105 reside. In response to received sounds transmitted by the middle ear 103, the fluid-filled cochlea 104 functions as a transducer to generate electric pulses which are transmitted to the cochlear nerve 105, and ultimately to the brain.

Hearing is impaired when there are problems in the ability to transduce external sounds into meaningful action potentials along the neural substrate of the cochlea 104. To improve impaired hearing, hearing prostheses have been developed. For example, when the impairment is related to operation of the middle ear 103, a conventional hearing aid or middle ear implant may be used to provide acoustic-mechanical stimulation to the auditory system in the form of amplified sound. Or when the impairment is associated with the cochlea 104, a cochlear implant with an implanted stimulation electrode can electrically stimulate auditory nerve tissue with small currents delivered by multiple electrode contacts distributed along the electrode.

Middle ear implants employ electromagnetic transducers to convert sounds into mechanical vibration of the middle ear 103. A coil winding is held stationary by attachment to a non-vibrating structure within the middle ear 103 and microphone signal current is delivered to the coil winding to generate an electromagnetic field. A magnet is attached to an ossicle within the middle ear 103 so that the magnetic field of the magnet interacts with the magnetic field of the coil. The magnet vibrates in response to the interaction of the magnetic fields, causing vibration of the bones of the middle ear 103. See U.S. Pat. No. 6,190,305, which is incorporated herein by reference.

U.S. Pat. No. 8,246,532 (incorporated herein by reference in its entirety) described another type of implantable hearing prosthesis system which uses bone conduction to deliver an audio signal to the cochlea for sound perception in persons with conductive or mixed conductive/sensorineural hearing loss. An implanted floating mass transducer (FMT) is affixed to the temporal bone. In response to an externally generated electrical audio signal, the FMT couples a mechanical stimulation signal to the temporal bone for delivery by bone conduction to the cochlea for perception as a sound signal. A certain amount of electronic circuitry must also be implanted with the FMT to provide power to the implanted device and at least some signal processing which is needed for converting the external electrical signal into the mechanical stimulation signal and mechanically driving the FMT.

Most existing bone conduction systems use two standard bone screws to attach the transducer to the patient's skull bone. This screw fixation arrangement requires additional space, additional parts, and additional bone drilling (a longer surgical procedure). When the screw holes are not very precise or if the skull bone lacks the appropriate structure, these attachment screws may not sit very well.

U.S. Pat. No. 8,241,201 describes various bone conduction transducer arrangements including an embodiment with a non-screw fixation mechanism where an adaptor made of biocompatible material is placed between the bottom of the transducer housing and the underlying bone. WO 2014138149 describes various different fixation features on the outer perimeter of a cochlear implant housing. U.S. Pat. No. 8,909,348 also shows a cochlear implant with stabilizing projections on its outer perimeter. U.S. Pat. No. 7,937,156 shows another cochlear implant housing with various osseointegrating projections.

SUMMARY

Embodiments of the present invention are directed to an implantable bone conduction transducer with a center rotational axis radially surrounded by an outer surface, and at least one radial projection projecting radially outward from the outer surface. An implantable transducer receptacle has a receptacle outer surface configured to fit into a receptacle recess in skull bone of a recipient patient, a receptacle inner surface configured to fit around the outer surface of the transducer, and at least one projection bracket projecting radially inward away from the receptacle inner surface. The at least one projection bracket and the at least one radial projection are configured to cooperate so that rotation of the transducer around the center rotational axis creates increased lateral force between the transducer and the skull bone surrounding the receptacle recess so as to securely engage the transducer with the skull bone.

In specific embodiments, the at least one projection bracket may be configured to deform in response to the rotation of the transducer to form a lip of projection bracket material rotationally behind the at least one radial projection that resists counter-rotation of the transducer that would reduce the lateral force. In addition or alternatively, the outer surface of the at least one radial projection and the inner surface of the at least one projection bracket may have one or more counter-rotation resistance features configured to cooperate to resist counter-rotation of the transducer that would reduce the lateral force. For example, the counter-rotation resistance features may be cooperating ratchet teeth, one or more surface regions of increased surface roughness, and/or one or more surface regions with high friction coating configured to resist counter-rotation of the transducer.

There may also be one or more outer rings that surround the receptacle outer surface configured to hold together the transducer receptacle; for example, made of silicone material. The transducer may include an end surface with a surface treatment for promoting osseointegration of the end surface with adjacent skull bone. The upper end of the transducer may include a rotation promotion feature configured to cooperate with a surgical instrument to facilitate the rotation of the transducer around the center rotational axis to create the increased lateral force.

In specific embodiments, the projection bracket may be made of a biocompatible polymer material or titanium. The transducer may have multiple radial projections, which may be all equal in size or different sizes. There may be multiple projection brackets, which may be all equal in size or different sizes.

DETAILED DESCRIPTION

Embodiments of the present invention are directed to arrangements for fixing a bone conduction transducer such as an FMT to an implanted patient's skull bone by directing a lateral clamping force against the bone recess which receives the transducer. Such arrangements avoid the conventional need for bone cement and bone screws and all the related requirements such as a drill template, seats, drill, etc. The depth of the transducer bone bed also can be reduced (e.g., to 2 mm if necessary) without the need for seats so preparing the bone bed is less complicated. In addition, a relatively high lateral clamping force can be applied to the bone so that osseointegration of the transducer site is not mandatory. And, the lateral force approach does not increase the height of the transducer arrangement (as opposed to other approaches such in U.S. Pat. No. 8,241,201).

Figure 1:
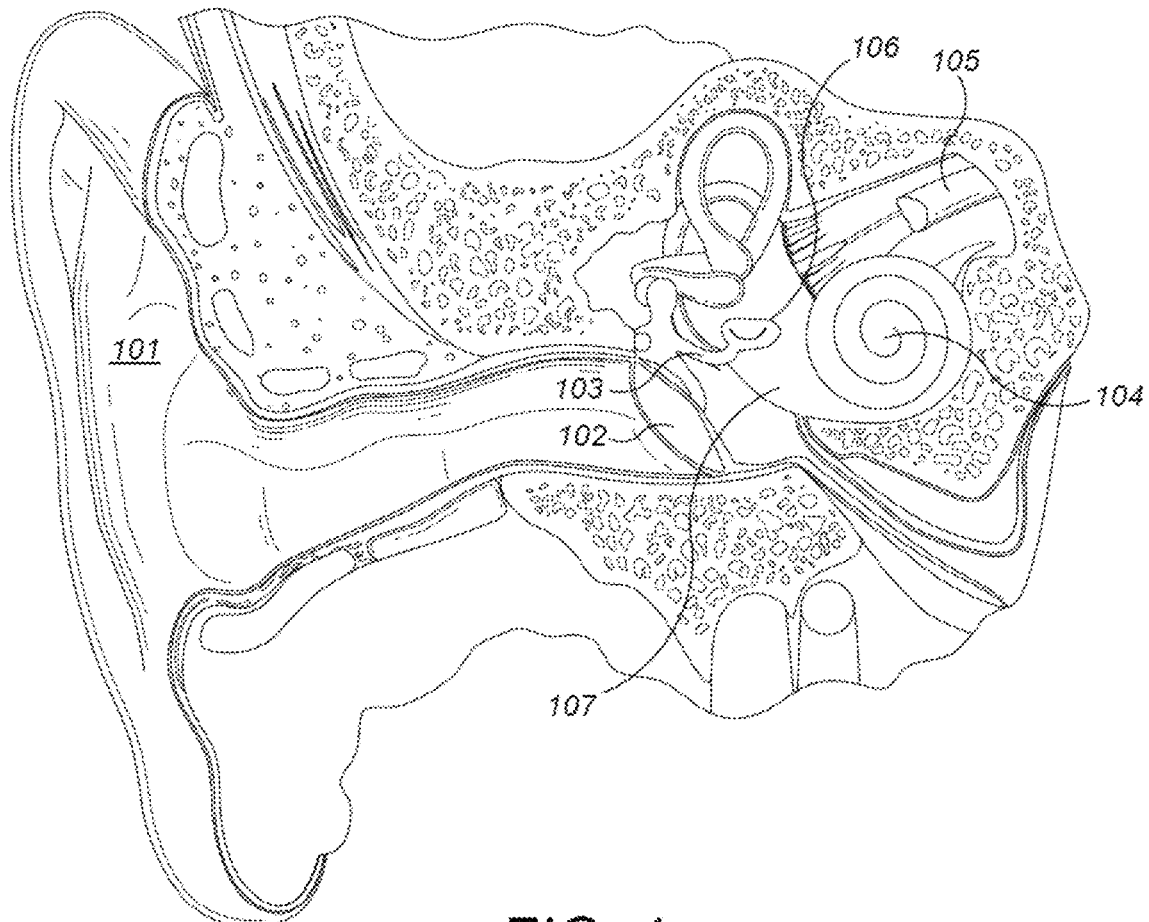
FIG. 1 shows anatomical structures of a typical human ear.
Figure 2:
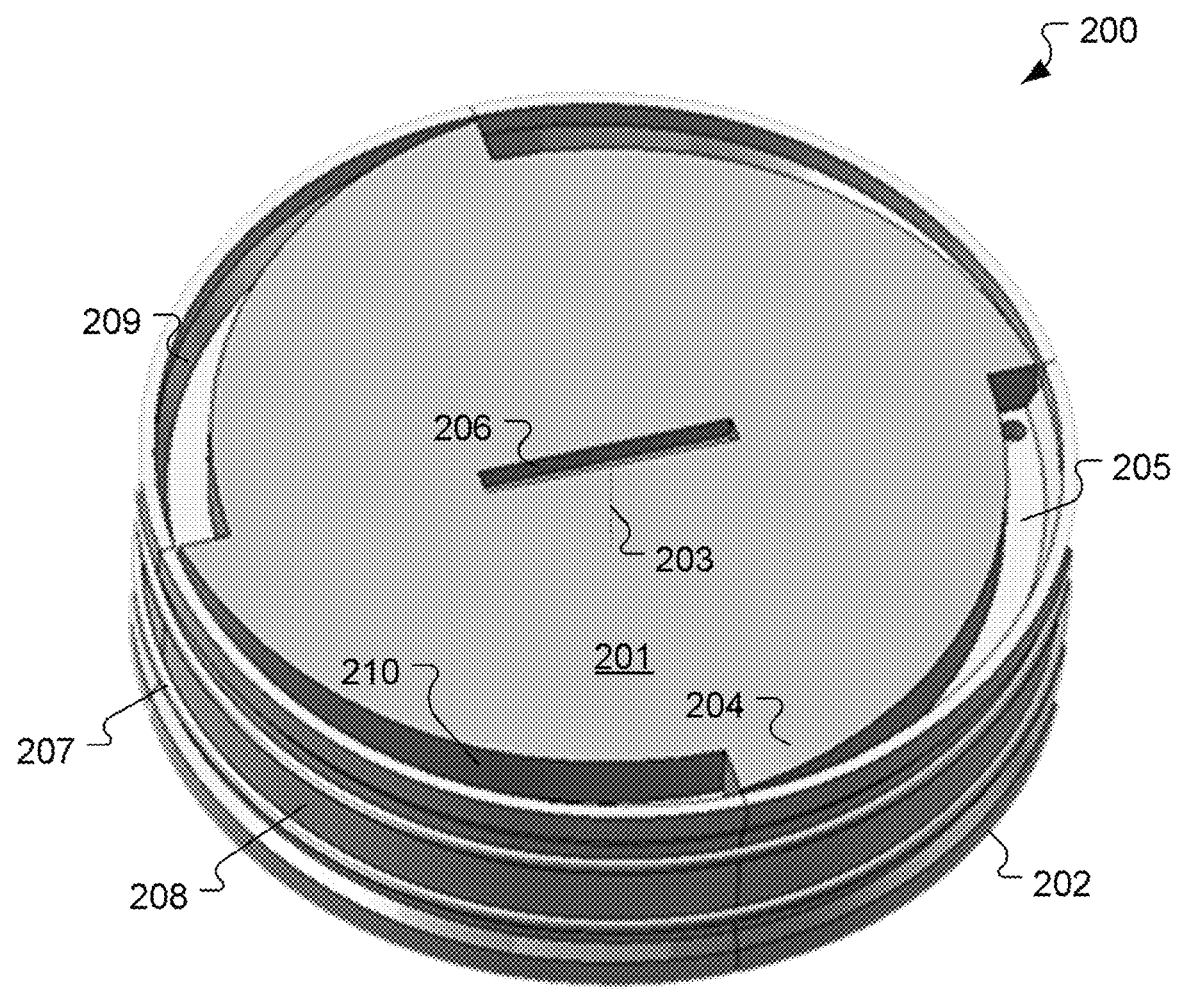
FIG. 2 shows an elevated perspective view of an implantable bone conduction transducer arrangement according to an embodiment of the present invention.

FIG. 2 shows an elevated perspective top view of an implantable bone conduction transducer arrangement 200 which includes an implantable bone conduction transducer 201 with a center rotational axis 203 that is radially surrounded by an outer surface 210. The outer surface 210 of the transducer 201, either as a whole or in part—e.g. the lower end of the transducer 201, has one or more radial projections 204 that project radially outward progressively increasing in radial distance from the center rotational axis 203; e.g., increasing about 2 mm. In this specific instance there are four symmetrically arranged equal size radial projections 204, though in other embodiments, the radial projections 204 may be different sizes and/or distributed around the outer surface 210 in different asymmetric geometries.

The upper surface of the transducer 201 may also include one or more rotation promotion features, in this case, there is a screwdriver blade slot 206 that is configured to cooperate with a surgical instrument (screwdriver) to facilitate the rotation of the transducer 201 around the center rotational axis 203. To facilitate future explantation capability, in specific embodiments some or all of the outer surfaces of the transducer arrangement 200 may be surface treated to prevent osseointegration with the adjacent bone tissue. Such surface treatment should resist the mechanical forces that can arise when structural elements of the transducer arrangement 200 move relative to each other when rotating the transducer 201 during implantation surgery. On the other hand, it may be advantageous if some selected areas of the transducer arrangement 200 are allowed to osseointegrate with the adjacent bone tissue for long term secure fixation of the transducer 201 within the surrounding bone. Thus one or more surfaces of the transducer 201 may receive a surface treatment for promoting osseointegration of the treated surface with adjacent skull bone—e.g., there are many such commercially available treatments for dental implants.

An implantable transducer receptacle 202 has a receptacle outer surface 208 that is configured to fit into a receptacle recess in skull bone of a recipient patient. The transducer receptacle 202 also has a receptacle inner surface 209 that is configured to fit around the outer surface 210 of the transducer 210. The transducer receptacle 202 includes one or more projection brackets 205 made of titanium or biocompatible polymer material that project radially inward away from the receptacle inner surface 209.

In the embodiment shown in FIG. 2, there also are outer containing rings 207 that surround the receptacle outer surface 208 and that are configured to hold together the transducer receptacle 202 before the arrangement is inserted into the bone bed in the skull bone. The containing rings 207 may be made of medical grade silicone material which is inexpensive and easy to work with during manufacturing. Once the transducer arrangement 200 is inserted, the containing rings 207 are no longer needed, but they may remain where they are. The silicone containing rings 207 are flexible enough that they do not prevent or adversely affect the rotation functionality described below. Alternatively, the containing rings 207 may be removed before rotating the inserted transducer 201.

The projection brackets 205 and the radial projections 204 are configured to cooperate so that rotation of the transducer 201 around the center rotational axis 203 creates increased lateral force between the transducer 201 and the skull bone surrounding the transducer receptacle 202 so as to securely engage the transducer 201 with the skull bone. Thus, in the specific embodiment shown in FIG. 2, there are four symmetrically arranged equal size projection brackets 205 to match and correspond with the four radial projections 204 of the transducer 201. Of course, in other specific embodiments, the projection brackets 205 may be different sizes and/or distributed around the transducer receptacle 202 in different asymmetric geometries that match and correspond to the radial projections 204 of the transducer 201.

Figure 3A:
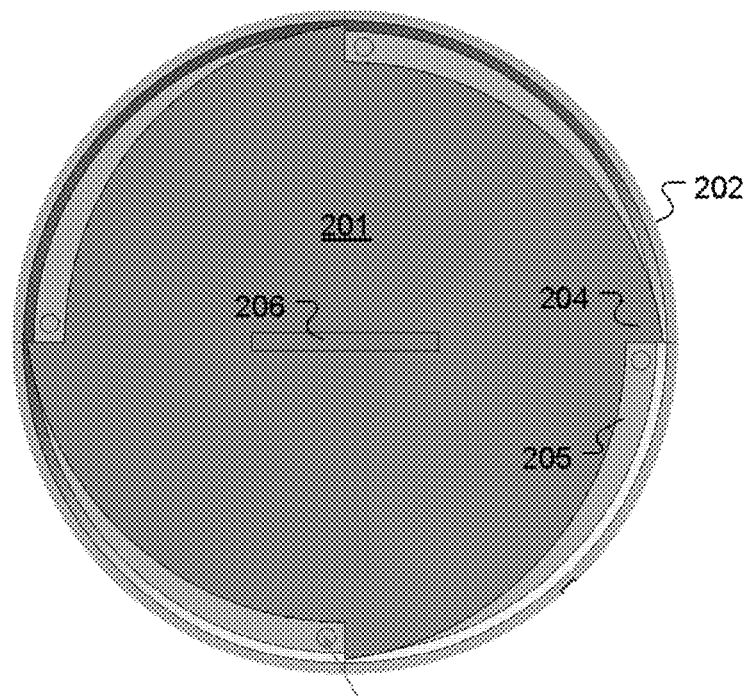
FIGS. 3A-3B show top cross-sectional views of the arrangement in FIG. 2 when rotated to create increased lateral force according to an embodiment of the present invention.
Figure 3B:
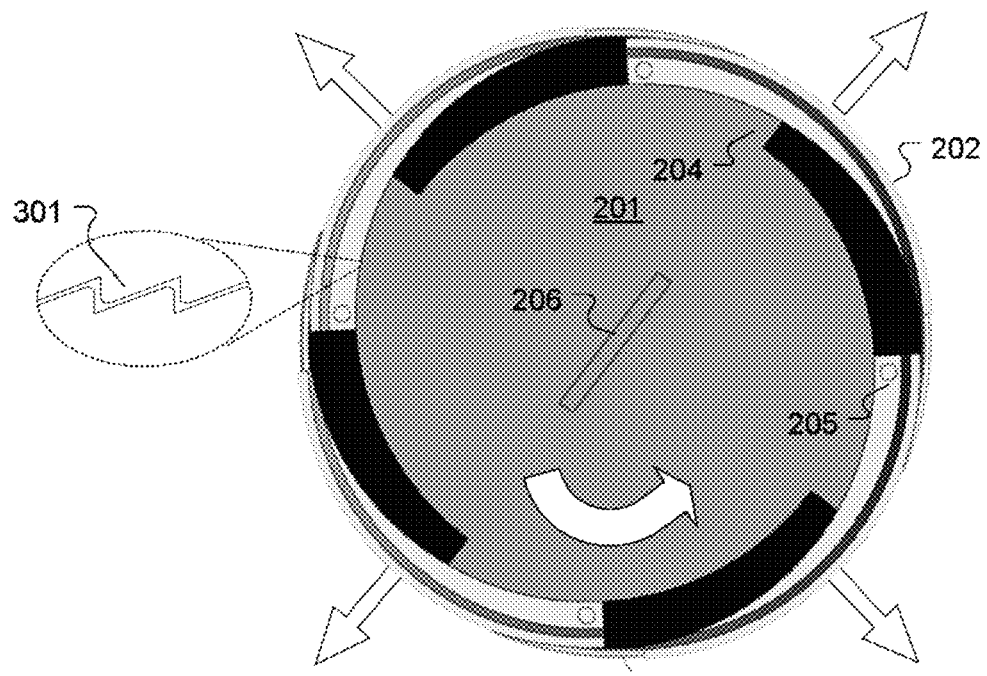

FIGS. 3A-3B show top cross-sectional views of the bone conduction transducer arrangement 200 shown in FIG. 2, when rotated to create increased lateral force. The view in FIG. 3A shows the initial unrotated position of the transducer 201 and its radial projections 204 with respect to the transducer receptacle 202 and its corresponding projection brackets 205. Before the surgical insertion of the transducer arrangement 200, a transducer bed is prepared in the skull bone of the insertion site. The footprint of the transducer bed needs to be slightly larger than the footprint of the transducer arrangement 200. The depth of the prepared bone bed may be equal to, greater than, or less than the height of the transducer arrangement 200.

Once the bone conduction transducer arrangement 200 has been surgically inserted into the prepared bone recess in the patient's skull bone, the surgeon rotates the transducer 201 as shown in FIG. 3B. When the transducer 201 is rotated, the radial projections 204 and the corresponding projection brackets 205 interact to create increased lateral force between the transducer 201 and the skull bone surrounding the transducer receptacle 202 so as to securely engage the transducer 201 with the skull bone. the geometry of the projection brackets 205 and the other structures may be controlled so as to limit the maximum lateral force that can be created (e.g., by allowing deformation of the projection brackets 205). If a portion of the transducer 201 is prepared to osseointegrate with the skull bone, then the lateral fixation force provided by the rotation of the transducer 201 is only needed for an initial period after implantation, e.g. the first two weeks.

The outer surface of the radial projections 204 and the inner surface of the projection brackets 205 also may have one or more counter-rotation resistance features that are configured to cooperate to resist counter-rotation of the transducer 201 that would reduce the lateral force. In the embodiment shown in FIG. 3B, the counter-rotation resistance features are cooperating ratchet teeth 301, in other embodiments there may be one or more surface regions of increased surface roughness and/or one or more surface regions with high friction coating configured to resist counter-rotation of the transducer. In addition or alternatively, the projection brackets 205 may be configured to deform in response to the rotation of the transducer 201 to form a lip of projection bracket material that is rotationally behind the rotating radial projection 204 that resists counter-rotation of the transducer 201.

Figure 4A:
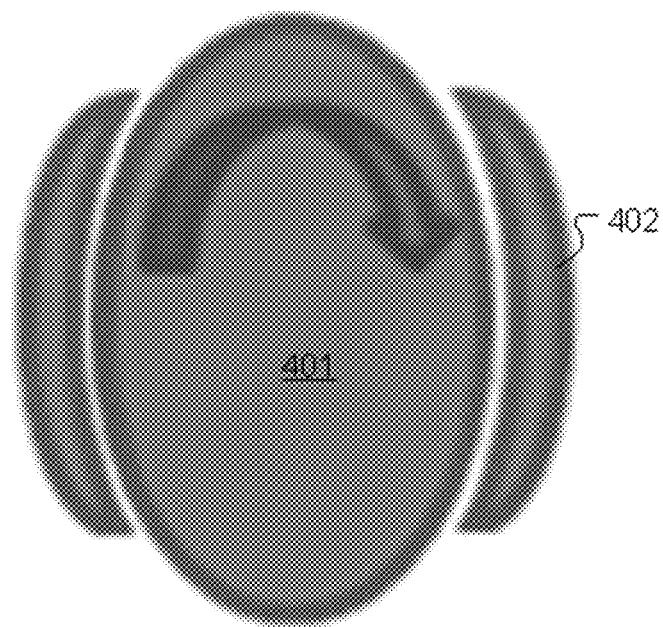
FIGS. 4A-4B show simplified top cross-sectional views of an embodiment with an oval shaped transducer.
Figure 4B:
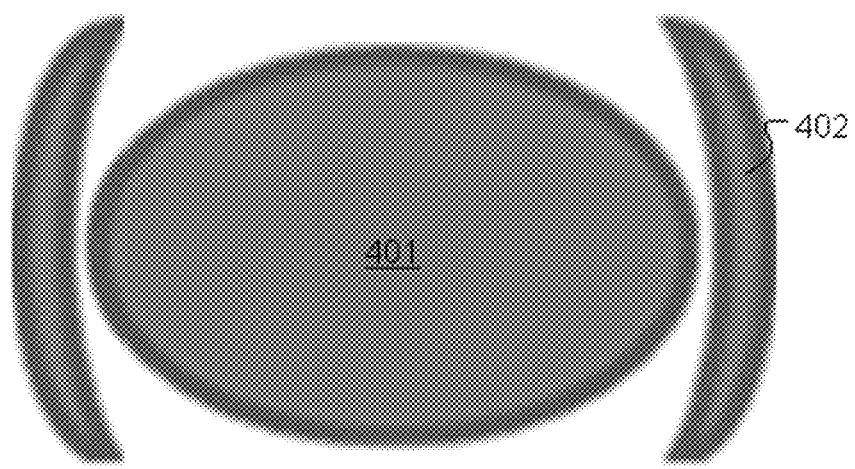

In the specific embodiments described above, the transducer is generally cylindrical in shape, but that is not necessarily the case in every embodiment. For example, FIGS. 4A-4B show simplified top cross-sectional views of an embodiment with an oval shaped transducer 401 that rotates to create increased lateral force with one or more surrounding receptacle brackets 402. And as evident from FIGS. 4A-4B, it is not necessarily the case that the projection brackets 402 entirely surround the transducer 401.

Although various exemplary embodiments of the invention have been disclosed, it should be apparent to those skilled in the art that various changes and modifications can be made which will achieve some of the advantages of the invention without departing from the true scope of the invention.

What is claimed is:

1. An implantable bone conduction transducer arrangement comprising:
   an implantable bone conduction transducer including:
      i. a center rotational axis radially surrounded by an outer surface, and
      ii. at least one radial projection projecting radially outward from the outer surface;
   an implantable transducer receptacle including:
      i. a receptacle outer surface configured to fit into a receptacle recess in skull bone of a recipient patient,
      ii. a receptacle inner surface configured to fit around the outer surface of the transducer, and
      iii. at least one projection bracket projecting radially inward away from the receptacle inner surface;
   wherein the at least one radial projection progressively increases in radius in the rotational direction and is configured to interact with the at least one projection bracket so that rotation of the transducer around the center rotational axis creates increased lateral force between the transducer and the skull bone surrounding the receptacle recess so as to securely engage the transducer with the skull bone.

2. The implantable bone conduction transducer arrangement according to claim 1, wherein the at least one projection bracket is configured to deform in response to the rotation of the transducer to form a lip of projection bracket material rotationally behind the at least one radial projection that resists counter-rotation of the transducer that would reduce the lateral force.

3. The implantable bone conduction transducer arrangement according to claim 1, wherein an outer surface of the at least one radial projection and an inner surface of the at least one projection bracket have one or more counter-rotation resistance features configured to cooperate to resist counter-rotation of the transducer that would reduce the lateral force.

4. The implantable bone conduction transducer arrangement according to claim 3, wherein the one or more counter-rotation resistance features include a plurality of cooperating ratchet teeth configured to resist counter-rotation of the transducer.

5. The implantable bone conduction transducer arrangement according to claim 3, wherein the one or more counter-rotation resistance features include surface regions of increased surface roughness configured to resist counter-rotation of the transducer.

6. The implantable bone conduction transducer arrangement according to claim 3, wherein the one or more counter-rotation resistance features include surface regions with high friction coating configured to resist counter-rotation of the transducer.

7. The implantable bone conduction transducer arrangement according to claim 1, further comprising:
   at least one outer ring surrounding the receptacle outer surface configured to hold together the transducer receptacle.

8. The implantable bone conduction transducer arrangement according to claim 7, wherein the at least one outer ring is made of silicone material.

9. The implantable bone conduction transducer arrangement according to claim 1, wherein the transducer includes an end surface with a surface treatment for promoting osseointegration of the end surface with adjacent skull bone.

10. The implantable bone conduction transducer arrangement according to claim 1, wherein the transducer includes an upper surface with a rotation promotion feature configured to cooperate with a surgical instrument to facilitate the rotation of the transducer around the center rotational axis to create the increased lateral force.

11. The implantable bone conduction transducer arrangement according to claim 1, wherein the at least one projection bracket is made of a biocompatible polymer material.

12. The implantable bone conduction transducer arrangement according to claim 1, wherein the at least one projection bracket is made of titanium.

13. The implantable bone conduction transducer arrangement according to claim 1, wherein the transducer has a plurality of radial projections.

14. The implantable bone conduction transducer arrangement according to claim 13, wherein the radial projections are all equal in size.

15. The implantable bone conduction transducer arrangement according to claim 13, wherein the radial projections have different sizes.

16. The implantable bone conduction transducer arrangement according to claim 1, wherein the receptacle inner surface has a plurality of projection brackets.

17. The implantable bone conduction transducer arrangement according to claim 16, wherein the projection brackets are all equal in size.

18. The implantable bone conduction transducer arrangement according to claim 16, wherein the projection brackets have different sizes.

* * * * *